(12) United States Patent
Tomita et al.

(10) Patent No.: US 9,395,336 B2
(45) Date of Patent: Jul. 19, 2016

(54) SCANNING ACOUSTIC TOMOGRAPH

(71) Applicant: Hitachi Power Solutions Co., Ltd., Hitachi-shi, Ibaraki (JP)

(72) Inventors: Takashi Tomita, Hitachi (JP); Hirokazu Nagaoka, Hitachi (JP); Kaoru Kitami, Hitachi (JP); Masafumi Takada, Hitachi (JP)

(73) Assignee: Hitachi Power Solutions Co., Ltd., Hitachi-shi (JP)

( * ) Notice: Subject to any disclaimer, the term of this patent is extended or adjusted under 35 U.S.C. 154(b) by 271 days.

(21) Appl. No.: 14/261,000

(22) Filed: Apr. 24, 2014

(65) Prior Publication Data

US 2014/0318252 A1 Oct. 30, 2014

(30) Foreign Application Priority Data

Apr. 25, 2013 (JP) ................................. 2013-092254

(51) Int. Cl.
*G01N 24/00* (2006.01)
*G01N 29/00* (2006.01)
*G01N 29/04* (2006.01)
*G01N 29/06* (2006.01)
*G01N 29/11* (2006.01)
*G01N 29/265* (2006.01)
*G01N 29/28* (2006.01)

(52) U.S. Cl.
CPC ............ *G01N 29/0672* (2013.01); *G01N 29/11* (2013.01); *G01N 29/265* (2013.01); *G01N 29/28* (2013.01); *G01N 2291/048* (2013.01)

(58) Field of Classification Search
CPC . G01N 29/0672; G01N 29/11; G01N 29/265; G01N 2291/048
USPC ........................................................... 73/625
See application file for complete search history.

(56) References Cited

U.S. PATENT DOCUMENTS 3,848,460 A * 11/1974 Bantz ....................... G01H 5/00
73/597
3,930,404 A * 1/1976 Ryden, Jr. .............. G01B 17/02
73/610

FOREIGN PATENT DOCUMENTS

JP 2002-296247 A 10/2002

* cited by examiner

*Primary Examiner* — Lisa Caputo
*Assistant Examiner* — Roger Hernandez-Prewit
(74) *Attorney, Agent, or Firm* — Crowell & Moring LLP

(57) ABSTRACT

A scanning acoustic tomograph has a water tank which accommodates water, a sample stand which is disposed in the water tank and on which a subject is placed, a first ultrasonic transducer which irradiates ultrasonic waves toward the subject, and a second ultrasonic transducer which receives the ultrasonic waves transmitted through the subject, the first and second ultrasonic transducers are disposed opposed to each other in a vertical direction, and a hydrophilic film is formed on a lower surface side of the sample stand.

20 Claims, 13 Drawing Sheets

SCANNING ACOUSTIC TOMOGRAPH

BACKGROUND OF THE INVENTION

1. Field of the Invention

The present invention relates to a scanning acoustic tomograph, and more specifically, to a scanning acoustic tomograph which measures the internal part of a subject in a non-destructive manner using ultrasonic waves in water as an ultrasonic transmission medium, and displays an exploration video and the like of the subject or determines the acceptance of an internal defect.

2. Background Art

Scanning acoustic tomographs perform scanning by repeatedly performing the irradiation of ultrasonic waves toward a subject and the reception of the ultrasonic waves reflected or transmitted from the subject to express the intensities of the received ultrasonic waves as an image. Using properties in which the intensities of the ultrasonic waves reflected or transmitted from the subject are different from each other due to acoustic impedance of the respective parts of the subject, the scanning acoustic tomographs can examine the internal state of the subject in a non-destructive manner.

Since ultrasonic waves have such properties as to be difficult to transfer to a gas, scanning acoustic tomographs generally use water as an ultrasonic transmission medium to soak a subject and an ultrasonic transducer in the water to thus perform the examination.

As background art of this technical field, there is JP-A-2002-296247. JP-A-2002-296247 discloses that "the metal band is inserted between the ultrasonic transmitting element and the ultrasonic receiving element disposed opposed to each other in a water tank, and an ultrasonic beam is transmitted and received between the ultrasonic transmitting element and the ultrasonic receiving element via the metal band to detect an internal defect of the metal band" (see the abstract).

SUMMARY OF THE INVENTION

Since ultrasonic waves have such properties as to be difficult to transfer to a gas, there is a problem in that when bubbles adhere to a subject, the internal part of the subject in the part where the bubbles adhere cannot be examined. Moreover, when bubbles are confirmed in examination results after the ultrasonic examination, it is necessary to conduct the examination again after removal of the bubbles, and thus there is a problem in that the efficiency is significantly reduced.

In order to solve the problems, in the technology disclosed in JP-A-2002-296247, water in which bubbles are removed is supplied toward each of the clearance between the metal band and the ultrasonic transmitting element and the clearance between the metal band and the ultrasonic receiving element in the detection of the internal defect of the metal band. Accordingly, since the effect of the bubbles is eliminated, the internal defect due to ultrasonic flaw detection can be accurately detected.

However, when through transmission type scanning acoustic tomographs which perform examination by transmitting ultrasonic waves through a subject have a structure in which a sample stand on which the subject is placed is disposed in a water tank, the following problem occurs. That is, when the subject and the sample stand are dipped in the water, the air is trapped, and thus there is a concern that bubbles may remain on a lower surface of the sample stand. In this case, there is a concern that the bubbles remaining on the lower surface of the sample stand may immediately re-adhere to another place in the lower surface of the sample stand even when being scattered by a water flow, and when the bubbles are small, the bubbles are difficult to scatter with a water flow, and thus difficult to remove. Therefore, there is a problem in that due to the bubbles remaining on the lower surface of the sample stand, the ultrasonic waves transmitted through the subject cannot be received.

The invention is contrived in view of the above-described circumstances, and an object thereof is to provide a through transmission type scanning acoustic tomograph capable of removing bubbles remaining on a lower surface of a sample stand on which a subject is placed and of efficiently performing examination.

According to an aspect of the present invention, there is provided a scanning acoustic tomograph having a water tank which accommodates water, a sample stand which is disposed in the water tank and on which a subject is placed, and a first ultrasonic transducer which irradiates ultrasonic waves toward the subject and a second ultrasonic transducer which receives the ultrasonic waves transmitted through the subject, the first and second ultrasonic transducers disposed opposed to each other in a vertical direction, in which a hydrophilic film is formed on a lower surface side of the sample stand.

According to the invention, it is possible to provide a through transmission type scanning acoustic tomograph capable of removing bubbles remaining on a lower surface of a sample stand on which a subject is placed and of efficiently performing examination.

DETAILED DESCRIPTION OF THE INVENTION

Figure 1:
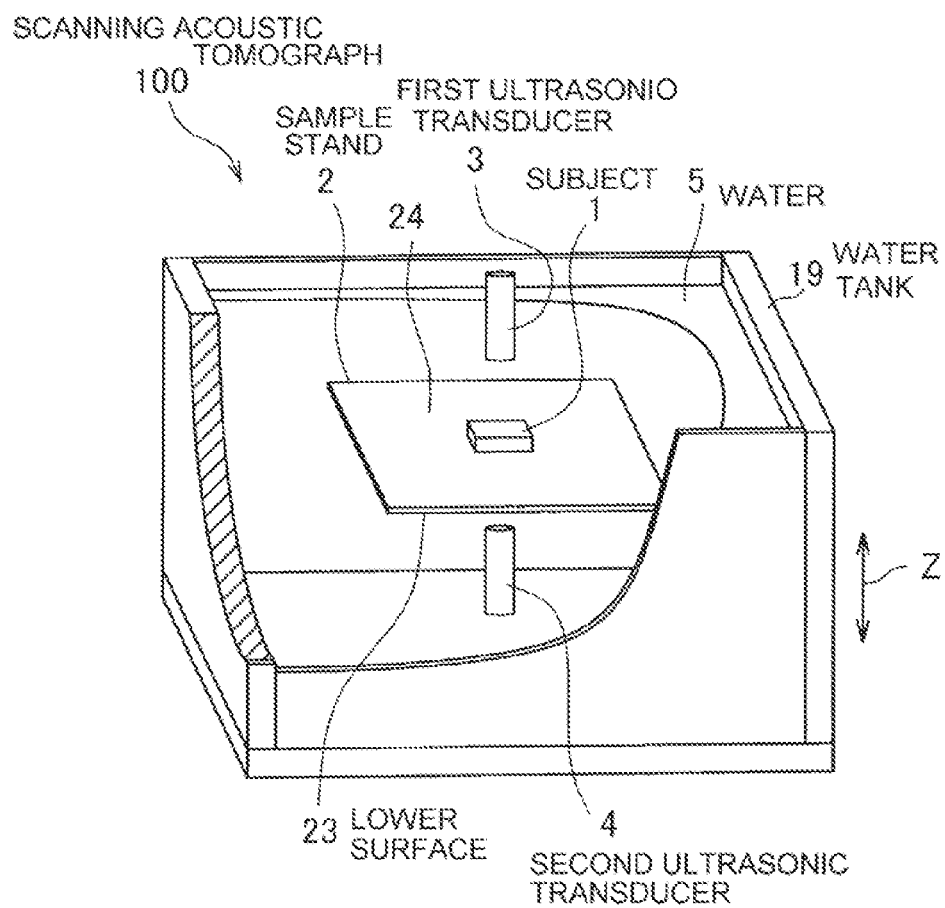
FIG. 1 is a partially cut-away perspective view schematically showing the appearance of a scanning acoustic tomograph according to a first embodiment of the invention.

Embodiments of the invention will be described in detail with appropriate reference to the drawings.

In the following drawings, the same or corresponding members will be denoted by the same reference numerals, and the repeated description will be appropriately omitted. The members may be varied or exaggerated in size and shape to be schematically expressed for the purpose of illustration.

First Embodiment

First, a scanning acoustic tomograph 100 according to a first embodiment of the invention will be described with reference to FIGS. 1 and 2.

FIG. 1 is a partially cut-away perspective view schematically showing the appearance of a scanning acoustic tomograph according to the first embodiment of the invention. FIG. 2 is a partially enlarged longitudinal sectional view of the sample stand shown in FIG. 1.

As shown in FIG. 1, the scanning acoustic tomograph 100 according to the first embodiment of the invention is a scanning acoustic tomograph which measures the internal part of a subject 1 in a non-destructive manner using ultrasonic waves in water 5 as an ultrasonic transmission medium, and displays an exploration video and the like of the subject 1 or determines the acceptance of an internal defect.

The scanning acoustic tomograph 100 has a water tank 19 which accommodates the water 5, a sample stand 2 which is disposed in the water tank 19 and on which the subject 1 is placed, and a first ultrasonic transducer 3 and a second ultrasonic transducer 4 which are disposed opposed to each other in a vertical direction (Z-direction). The first ultrasonic transducer 3 irradiates ultrasonic waves toward the subject 1, and the second ultrasonic transducer 4 receives the ultrasonic waves transmitted through the subject 1. The subject 1, the sample stand 2, the first ultrasonic transducer 3, and the second ultrasonic transducer 4 are dipped in the water 5 in the water tank 19 during the ultrasonic examination.

The sample stand 2 has a flat plate shape and is supported by a support member (not shown) in the water tank 19 to be disposed horizontally. The first ultrasonic transducer 3 and the second ultrasonic transducer 4 are disposed in the vertical direction so as to interpose the subject 1 therebetween, and are configured to be movable integrally in a horizontal direction by a driving device (not shown). The shape of the sample stand 2 is not limited to the rectangular plate shape, and may be, for example, a round plate shape. The shape of the water tank 19 is not limited to the rectangular box, and may be, for example, a cylindrical shape having a bottom.

Figure 2:
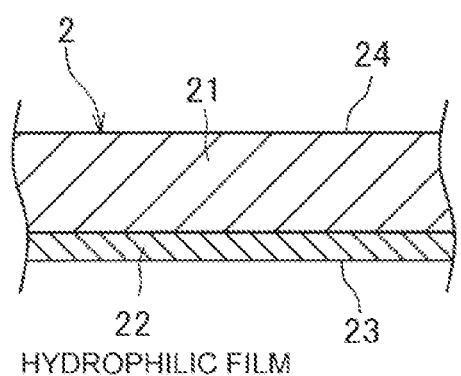
FIG. 2 is a partially enlarged longitudinal sectional view of the sample stand shown in FIG. 1.

As shown in FIG. 2, the sample stand 2 is provided with a substrate 21 and a hydrophilic film 22. That is, the hydrophilic film 22 having higher hydrophilicity than the substrate 21 is formed on a lower surface 23 of the sample stand 2. The substrate 21 is set to have a thickness of, for example, 2 mm to 10 mm to secure rigidity capable of stably supporting the subject 1 when the subject 1 is placed thereon. The hydrophilic film 22 is not particularly limited in thickness if its surface just has sufficient hydrophilicity. Here, the water contact angle of the surface of the hydrophilic film 22 is preferably 90 degrees or less, and more preferably 60 degrees or less.

Here, although a resin such as acryl is used as the material of the substrate 21 of the sample stand 2, the material is not limited thereto, and for example, glass, metal, and the like can be used. Here, although a silica-based glass film is used as the hydrophilic film 22, the hydrophilic film 22 is not limited thereto, and for example, a film made from cellulose nitrate, cellulose acetate (CA), polyamide (PA) or the like can be used. Examples of the method of forming the hydrophilic film 22 include a method of applying a coating agent, a method of attaching a film, a titanium oxide coating method through vacuum deposition, and a method of oxidizing a surface using oxygen plasma, and the same effects can be obtained even when any method is used.

Next, the action of the scanning acoustic tomograph 100 configured as described above will be described.

First, a subject 1 which is an examination object is manually or automatically placed on the sample stand 2 disposed in the water 5 in the water tank 19. In order to examine the internal part of the subject 1, the first ultrasonic transducer 3 and the second ultrasonic transducer 4 are horizontally moved with respect to the sample stand 2 to perform scanning over the subject 1.

Using properties in which the intensities of the ultrasonic waves transmitted through the subject 1 are different from each other due to acoustic impedance of the respective parts of the subject 1, the scanning acoustic tomograph 100 expresses the intensities of the received ultrasonic waves as an image. Accordingly, the internal state of the subject 1 can be examined in a non-destructive manner.

In this embodiment, the hydrophilic film 22 is formed on the lower surface 23 of the sample stand 2. Accordingly, the water 5 in the water tank 19 is stirred by, for example, the moving operations of the first ultrasonic transducer 3 and the second ultrasonic transducer 4 for examination of the internal part of the subject 1, and thus bubbles remaining even on the lower surface 23 of the sample stand 2 are easily removed. This is due to the reason that since the lower surface 23 of the sample stand 2 has good wettability with respect to the water 5 due to the formation of the hydrophilic film 22, it is difficult for bubbles to remain. Accordingly, it is possible to avoid a situation in which the internal part of the subject 1 in the part where the bubbles adhere cannot be examined.

That is, according to this embodiment, it is possible to provide a scanning acoustic tomograph 100 capable of removing bubbles remaining on the lower surface 23 of the sample stand 2 on which the subject 1 is placed and of efficiently performing examination.

A hydrophilic film may also be formed on an upper surface 24 of the sample stand 2. According to such a configuration, bubbles remaining on the upper surface 24 of the sample stand 2 are also easily removed.

Second Embodiment

Figure 3:
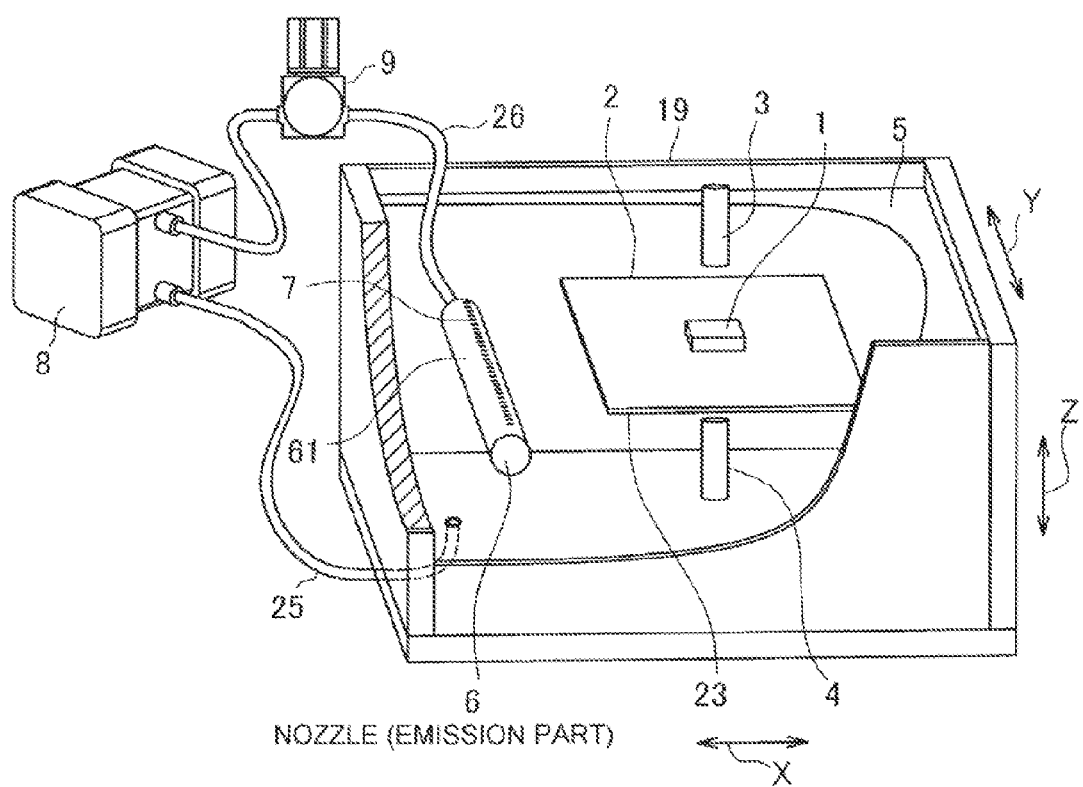
FIG. 3 is a partially cut-away perspective view schematically showing the appearance of a scanning acoustic tomograph according to a second embodiment of the invention.
Figure 4:
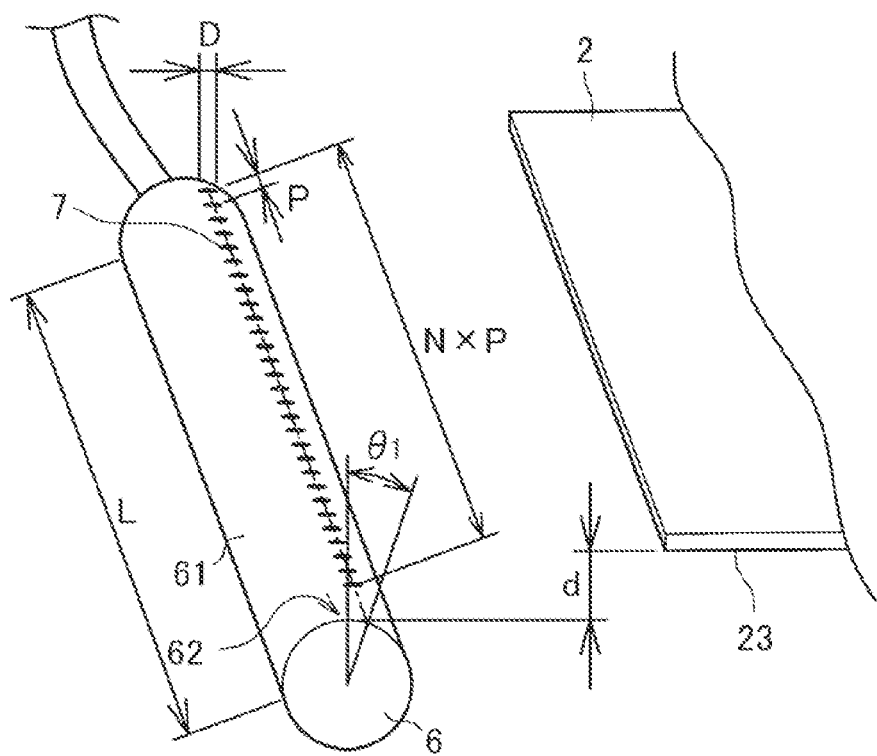
FIG. 4 is an enlarged perspective view of the nozzle shown in FIG. 3 and therearound.

Next, a scanning acoustic tomograph according to a second embodiment of the invention will be described with reference to FIGS. 3 and 4 by focusing on differences from the above-described first embodiment, and the description regarding the common points will be appropriately omitted. FIG. 3 is a partially cut-away perspective view schematically showing the appearance of a scanning acoustic tomograph according to the second embodiment of the invention. FIG. 4 is an enlarged perspective view of the nozzle shown in FIG. 3 and therearound.

As shown in FIG. 3, the scanning acoustic tomograph according to the second embodiment has a nozzle 6 as an emission part which emits water 5 toward a lower surface 23 of a sample stand 2. In addition, the scanning acoustic tomograph according to the second embodiment is provided with a pump 8 for circulating the water 5 in a water tank 19 and a pressure adjuster 9 which adjusts the pressure of the water 5 sent to the nozzle 6. The inside of the water tank 19 and the pump 8 are connected via a pipe 25, and the pump 8 and the nozzle 6 are connected via a pipe 26. The pressure adjuster 9 is installed, for example, in the middle of the pipe 26.

As shown in FIG. 4, the nozzle 6 having a circular pipe shape which is blocked at the tip end side has a cylindrical surface 61. The cylindrical surface 61 has a plurality of emission holes 7 arranged in an axial direction of the nozzle 6. The emission hole 7 is positioned to be able to emit the water 5 to the lower surface 23 of the sample stand 2. Specifically, the emission hole 7 is formed at an angular position inclined to the right in an X-direction in FIG. 3, that is, to the sample stand 2 by an angle $\theta_1$ (emission angle $\theta_1$) in a circumferential direction with respect to an apex part 62 of the cylindrical surface 61.

In such a second embodiment, the water 5 is emitted from the emission holes 7 provided in the nozzle 6 by operating the pump 8. When the water 5 is emitted toward the lower surface 23 of the sample stand 2, a water flow is generated along the lower surface 23 of the sample stand 2, and bubbles remaining on the lower surface 23 can thus be more efficiently blown and removed. Moreover, as in the first embodiment, since a hydrophilic film 22 is formed on the lower surface 23 of the sample stand 2, it is difficult for the blown bubbles to re-adhere to the sample stand 2. After the operation of the nozzle 6, in order to examine the internal part of a subject 1, a first ultrasonic transducer 3 and a second ultrasonic transducer 4 are moved horizontally with respect to the sample stand 2 to perform scanning over the subject 1.

The emission angle $\theta_1$ of the water, a diameter D, a pitch P, and a number N of the emission holes 7, a distance d in a vertical direction (Z-direction) between the lower surface 23 of the sample stand 2 and the nozzle 6, and an entire length L of the nozzle 6 may be set to experimentally appropriate values, respectively, and are not particularly limited. The emission rate of the water 5 from the nozzle 6 can be adjusted by the diameter D of the emission hole 7, and can also be adjusted using the pressure adjuster 9.

Here, as shown in FIG. 3, the nozzle 6 is disposed in parallel with the sample stand 2 in a depth direction (Y-direction), but is not limited thereto. The nozzle 6 may be disposed in parallel in a transverse direction (X-direction).

In addition, the nozzle 6 may be configured to be movable with respect to the sample stand 2. According to such a configuration, the water 5 can be securely emitted over a wide range of the lower surface 23 of the sample stand 2, and thus bubbles remaining on the lower surface 23 can be more efficiently blown and removed.

Figure 5:
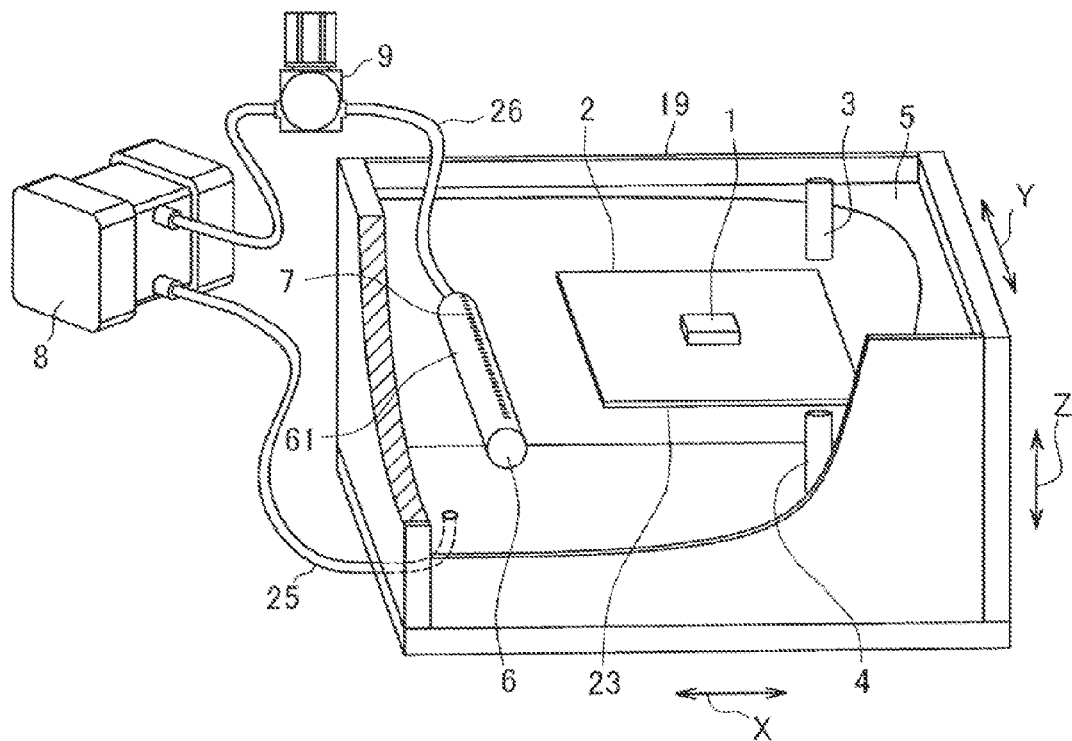
FIG. 5 is a perspective view of the appearance for illustrating the movement of the nozzle.

FIG. 5 is a perspective view of the appearance for illustrating the movement of the nozzle. As shown in FIG. 5, the first ultrasonic transducer 3 and the second ultrasonic transducer 4 are horizontally moved up to, for example, a predetermined evacuation position in an end part of the sample stand 2 during the movement of the nozzle 6. Accordingly, the interference between the nozzle 6 and the first and second ultrasonic transducers 3 and 4 can be avoided.

In FIG. 5, the nozzle 6 is configured so that it is disposed in parallel in the depth direction (Y-direction) and its position in the vertical direction (Z-direction) is fixed, whereby it is slidably movable in the transverse direction (X-direction), but the configuration is not limited thereto. For example, the nozzle 6 may be configured so that it is disposed in parallel in the transverse direction (X-direction) and its position in the vertical direction is fixed, whereby it is slidably movable in the depth direction (Y-direction). In addition, the nozzle 6 may be configured to be movable to an arbitrary position. An additional nozzle 6 may be installed to be able to emit the water 5 to an upper surface 24 of the sample stand 2. According to such a configuration, bubbles adhering to the upper surface 24 of the sample stand 2 and the subject 1 can be blown and removed.

Third Embodiment

Figure 6:
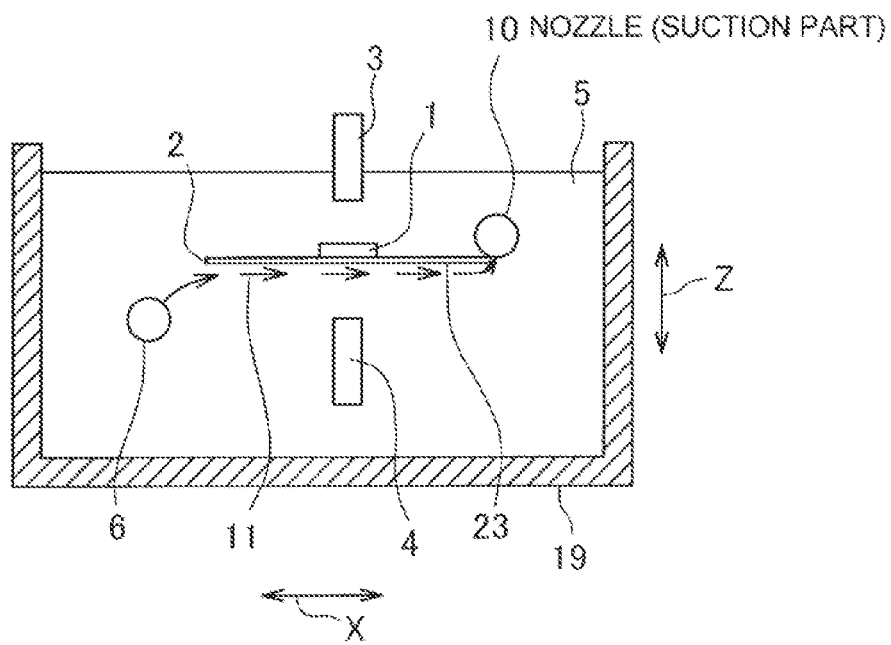
FIG. 6 is a longitudinal sectional view schematically showing a scanning acoustic tomograph according to a third embodiment of the invention.

Next, a scanning acoustic tomograph according to a third embodiment of the invention will be described with reference to FIG. 6 by focusing on differences from the above-described second embodiment, and the description regarding the common points will be appropriately omitted. FIG. 6 is a longitudinal sectional view schematically showing a scanning acoustic tomograph according to the third embodiment of the invention.

As shown in FIG. 6, the scanning acoustic tomograph according to the third embodiment is the same as the scanning acoustic tomograph according to the second embodiment shown in FIG. 3, except that a nozzle 10 is further provided as a suction part which sucks a fluid present on the side of a lower surface 23 of a sample stand 2.

According to such a third embodiment, a water flow 11 is generated by emitting water 5 from a nozzle 6 to suck bubbles blown due to the water flow 11 together with the water 5 from the suction nozzle 10, whereby the bubbles can be more securely removed from the lower surface 23 of the sample stand 2.

In addition, the nozzle 6 may be configured to be movable with respect to the sample stand 2. In this case, as shown in FIG. 7, during the movement of the nozzle 6, a first ultrasonic transducer 3 and a second ultrasonic transducer 4 are horizontally moved up to an evacuation position where the interference between the nozzle 6 and the first and second ultrasonic transducers 3 and 4 can be avoided.

Figure 7:
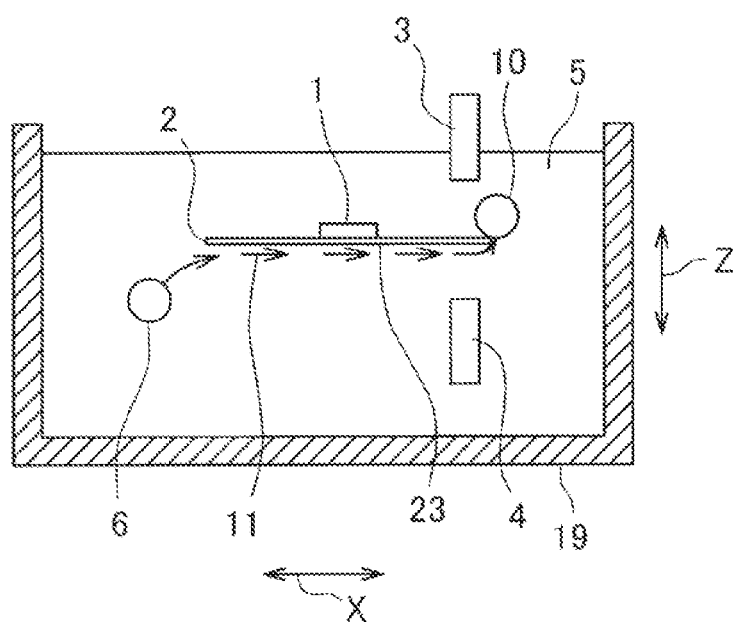
FIG. 7 is a longitudinal sectional view for illustrating the movement of a nozzle.
Figure 8:
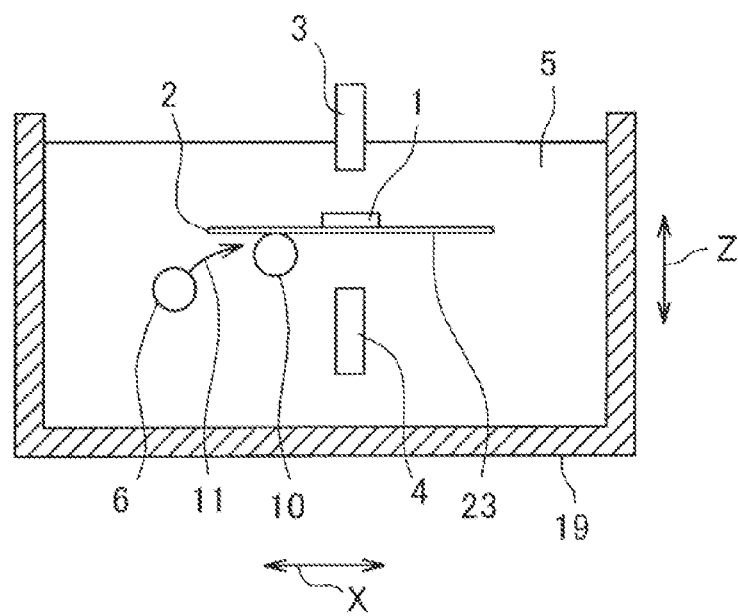
FIG. 8 is a longitudinal sectional view schematically showing a scanning acoustic tomograph in which a suction nozzle and an emission nozzle are configured to be movable in conjunction with each other.

As shown in FIGS. 6 and 7, the suction nozzle 10 is installed at an end part of the sample stand 2, and sucks the bubbles blown due to the water flow 11 at the end part of the sample stand 2. As shown in FIG. 8, a configuration in which the emission nozzle 6 and the suction nozzle 10 are disposed adjacent to each other so as to be opposed to each other and the suction nozzle 10 is movable with respect to the sample stand 2 in conjunction with the emission nozzle 6 may be employed. According to such a configuration, bubbles blown due to the water flow 11 can be immediately sucked, and thus bubbles can be more securely removed from the lower surface 23 of the sample stand 2.

Figure 9:
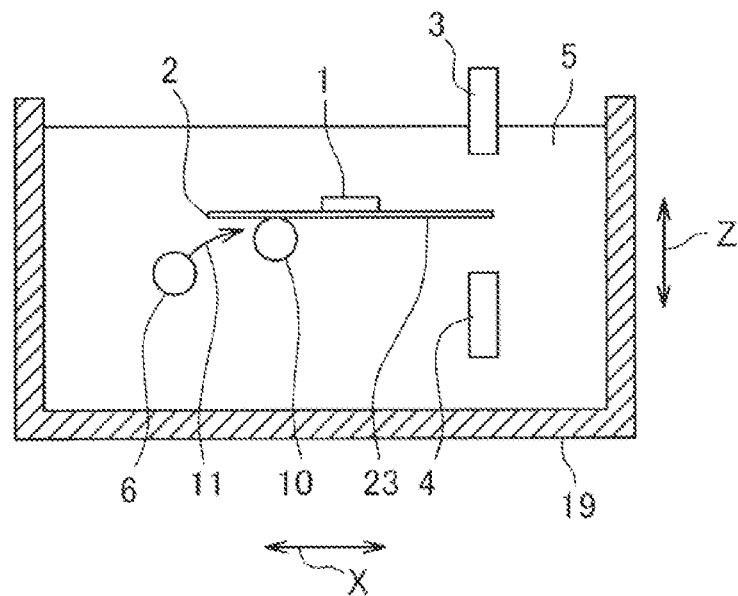
FIG. 9 is a longitudinal sectional view for illustrating the movement of the suction nozzle and the emission nozzle.

In this case, as shown in FIG. 9, during the movement of the nozzle 6 and the nozzle 10, the first ultrasonic transducer 3 and the second ultrasonic transducer 4 are horizontally moved up to an evacuation position where the interference between the nozzles 6 and 10 and the first and second ultrasonic transducers 3 and 4 can be avoided.

Fourth Embodiment

Figure 10:
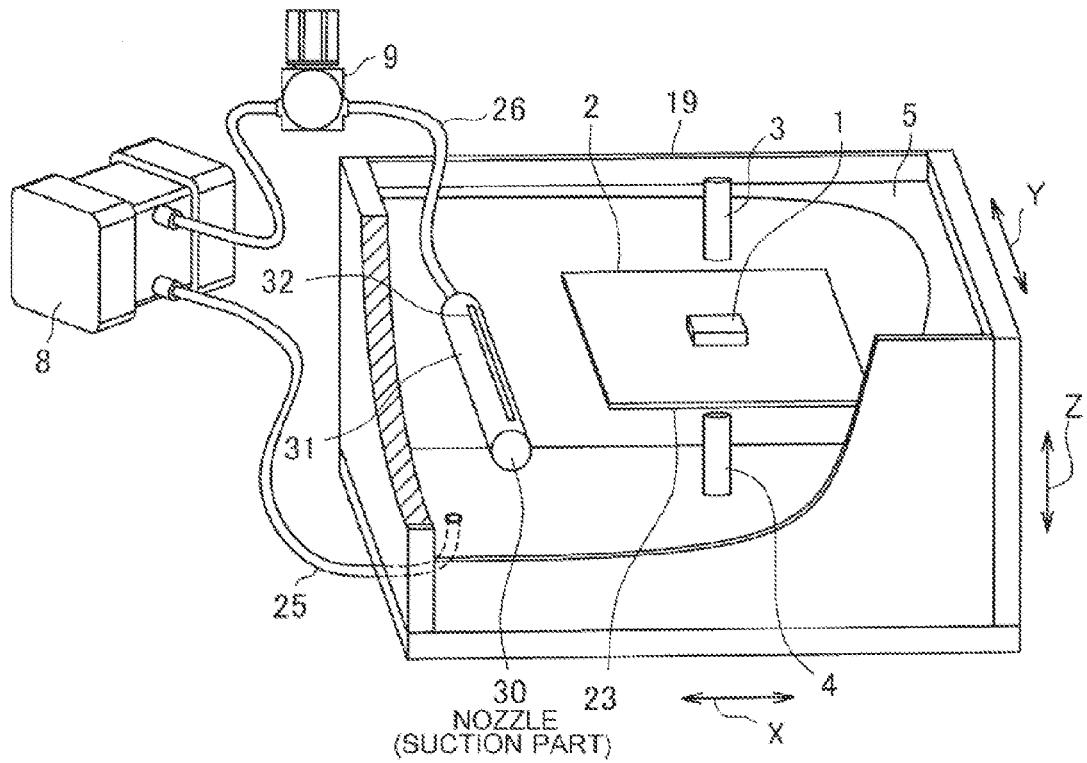
FIG. 10 is a partially cut-away perspective view schematically showing the appearance of a scanning acoustic tomograph according to a fourth embodiment of the invention.
Figure 11:
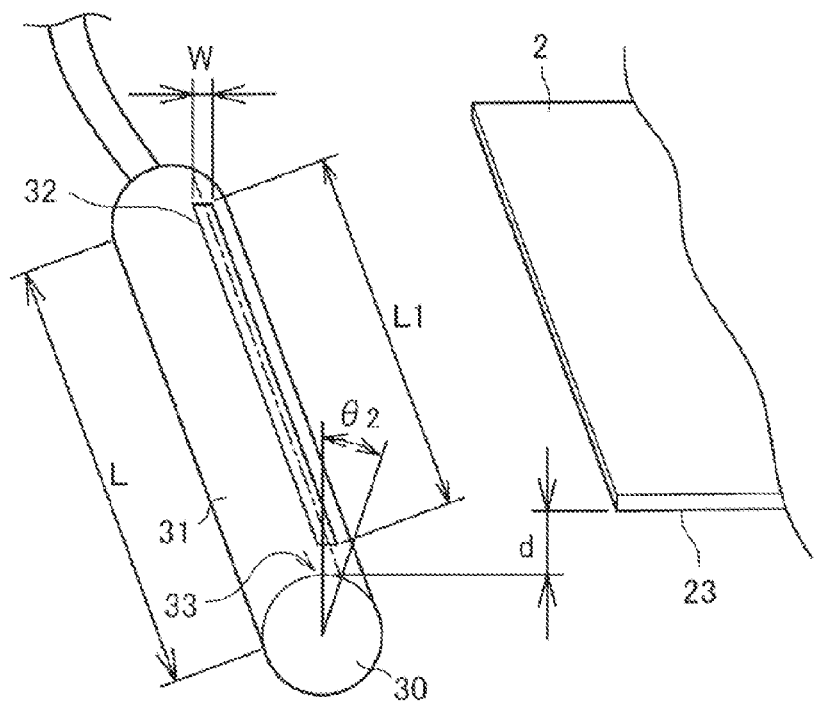
FIG. 11 is an enlarged perspective view of the nozzle shown in FIG. 10 and therearound.

Next, a scanning acoustic tomograph according to a fourth embodiment of the invention will be described with reference to FIGS. 10 and 11 by focusing on differences from the above-described first embodiment, and the description regarding the common points will be appropriately omitted. FIG. 10 is a partially cut-away perspective view schematically showing the appearance of a scanning acoustic tomograph according to the fourth embodiment of the invention. FIG. 11 is an enlarged perspective view of the nozzle shown in FIG. 10 and therearound.

As shown in FIG. 10, the scanning acoustic tomograph according to the fourth embodiment has a nozzle 30 as a suction part which sucks a fluid present on the lower surface side of a sample stand 2. In addition, the scanning acoustic tomograph according to the fourth embodiment is provided with a pump 8 for circulating water 5 in a water tank 19 and a pressure adjuster 9 which adjusts the pressure of the water 5 from the nozzle 30. The inside of the water tank 19 and the pump 8 are connected via a pipe 25, and the pump 8 and the nozzle 30 are connected via a pipe 26. The pressure adjuster 9 is installed, for example, in the middle of the pipe 26.

As shown in FIG. 11, the nozzle 30 having a circular pipe shape which is blocked at the tip end side has a cylindrical surface 31. The cylindrical surface 31 has an approximately rectangular suction hole 32 in which a longitudinal direction is parallel to an axial direction of the nozzle 30. The suction hole 32 is positioned to be able to suck a fluid present on the side of a lower surface 23 of the sample stand 2. Specifically, the suction hole 32 is formed at an angular position inclined to the right in an X-direction in FIG. 10, that is, to the sample stand 2 by an angle $\theta_2$ (suction angle $\theta_2$) in a circumferential direction with respect to an apex part 33 of the cylindrical surface 31.

In such a fourth embodiment, by operating the pump 8, the bubbles and the water 5 as a fluid present on the side of the lower surface 23 of the sample stand 2 are sucked from the suction hole 32 provided in the nozzle 30. When the bubbles are sucked from the suction hole 32, the bubbles remaining on the lower surface 23 can be more efficiently removed. Moreover, as in the first embodiment, since a hydrophilic film 22 is formed on the lower surface 23 of the sample stand 2, it is difficult for the bubbles separated from the lower surface 23 to re-adhere to the sample stand 2. After the operation of the nozzle 30, in order to examine the internal part of a subject 1, a first ultrasonic transducer 3 and a second ultrasonic transducer 4 are moved horizontally with respect to the sample stand 2 to perform scanning over the subject 1.

The suction angle $\theta_2$, a width W and a length L1 of the suction hole 32, a distance d in a vertical direction (Z-direction) between the lower surface 23 of the sample stand 2 and the nozzle 30, and an entire length L of the nozzle 30 may be set to experimentally appropriate values, respectively, and are not particularly limited.

Here, as shown in FIG. 10, the nozzle 30 is disposed in parallel with the sample stand 2 in a depth direction (Y-direction), but is not limited thereto. The nozzle 30 may be disposed in parallel in a transverse direction (X-direction).

In addition, the nozzle 30 may be configured to be movable with respect to the sample stand 2. According to such a configuration, bubbles can be securely sucked over a wide range of the lower surface 23 of the sample stand 2, and thus bubbles remaining on the lower surface 23 can be more efficiently removed.

Figure 12:
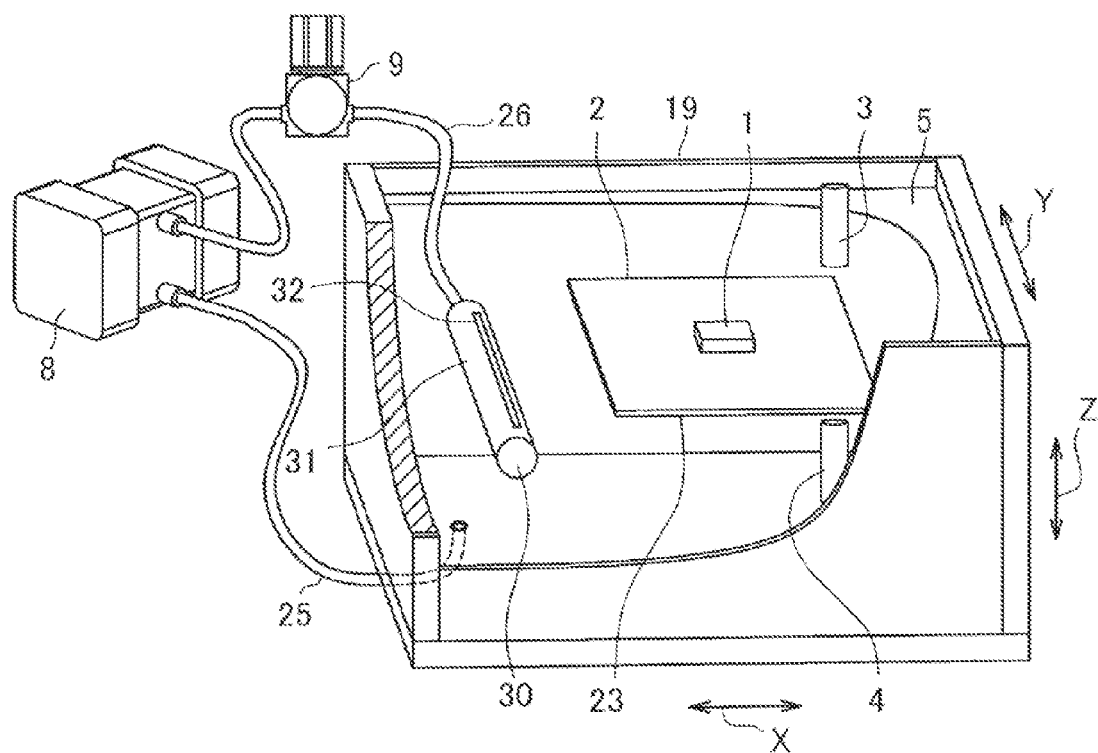
FIG. 12 is a perspective view of the appearance for illustrating the movement of the nozzle.

FIG. 12 is a perspective view of the appearance for illustrating the movement of the nozzle. As shown in FIG. 12, the first ultrasonic transducer 3 and the second ultrasonic transducer 4 are horizontally moved up to, for example, a predetermined evacuation position in an end part of the sample stand 2 during the movement of the nozzle 30. Accordingly, the interference between the nozzle 30 and the first and second ultrasonic transducers 3 and 4 can be avoided.

The fourth embodiment has the same configuration as that of the second embodiment in which the nozzle 6 is used as an emission nozzle, except that the nozzle 30 is used as a suction nozzle. Here, in place of the suction hole 32 having an approximately rectangular shape in FIG. 11 of the fourth embodiment, a plurality of holes may be formed as shown in FIG. 4 of the second embodiment. In place of the plurality of emission holes 7 in FIG. 4 of the second embodiment, a hole having an approximately rectangular shape may be formed as shown in FIG. 11 of the fourth embodiment.

Fifth Embodiment

Figure 13:
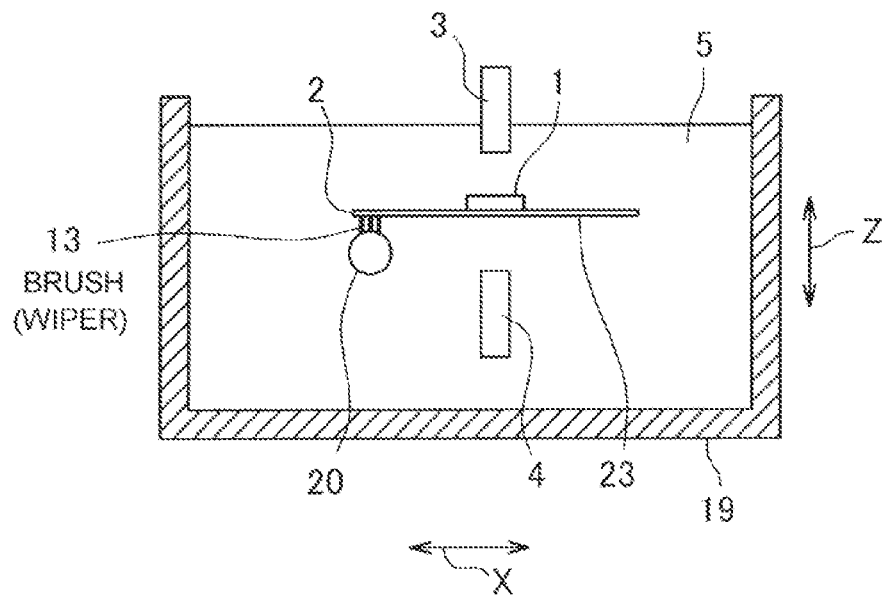
FIG. 13 is a longitudinal sectional view schematically showing a scanning acoustic tomograph according to a fifth embodiment of the invention.
Figure 14:
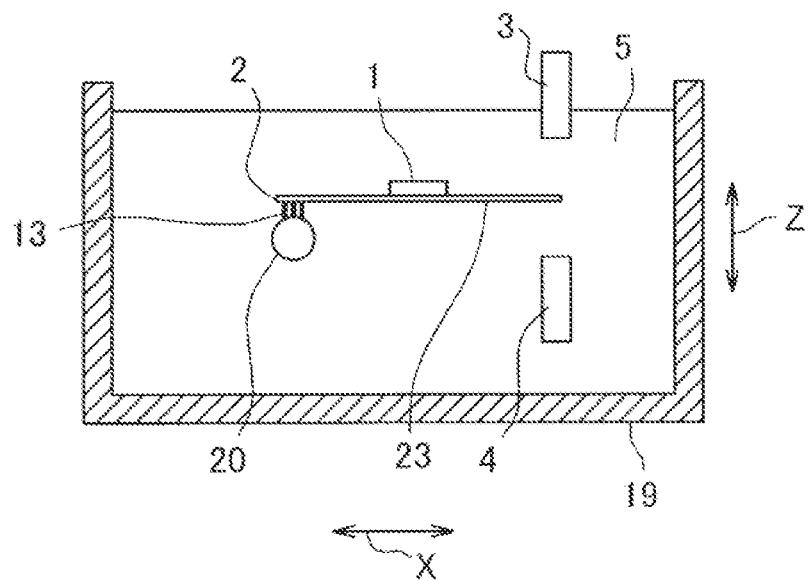
FIG. 14 is a perspective view of the appearance for illustrating the movement of a brush.

Next, a scanning acoustic tomograph according to a fifth embodiment of the invention will be described with reference to FIGS. 13 to 15F by focusing on differences from the above-described first embodiment, and the description regarding the common points will be appropriately omitted. FIG. 13 is a longitudinal sectional view schematically showing a scanning acoustic tomograph according to the fifth embodiment of the invention. FIG. 14 is a perspective view of the appearance for illustrating the movement of a brush. FIGS. 15A to 15F are enlarged views showing examples of a wiper.

Figure 15A:
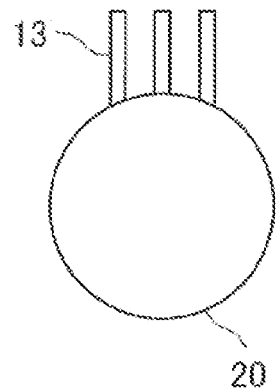
FIGS. 15A to 15F are enlarged views showing examples of a wiper.

As shown in FIG. 13, the scanning acoustic tomograph according to the fifth embodiment has a brush 13 as a wiper which is movable in contact with a lower surface 23 of a sample stand 2. As shown in FIGS. 13 and 15A, the brush 13 is erected to be arranged in an axial direction on an upper part of a bar member 20 having a columnar shape. Here, although a resin such as nylon is used as the material of the brush 13, the material is not limited thereto, and for example, animal hair and the like can be used.

In such a fifth embodiment, the brush 13 is directly brought into contact with the lower surface 23 of the sample stand 2 and the bar member 20 is horizontally moved in parallel with the sample stand 2, whereby bubbles can be brushed away and removed. Moreover, as in the first embodiment, since a hydrophilic film 22 is formed on the lower surface 23 of the sample stand 2, it is difficult for the brushed bubbles to re-adhere to the sample stand 2. After the operation of the bar member 20 with the brush 13, in order to examine the internal part of a subject 1, a first ultrasonic transducer 3 and a second ultrasonic transducer 4 are moved horizontally with respect to the sample stand 2 to perform scanning over the subject 1.

As shown in FIG. 13, the bar member 20 with the brush 13 is configured so that it is disposed in parallel in a depth direction (a direction perpendicular to the paper plane of FIG. 13) and its position in a vertical direction (Z-direction) is fixed, whereby it is slidably movable in a transverse direction (X-direction), but the configuration is not limited thereto. For example, the bar member 20 with the brush 13 may be configured so that it is disposed in parallel in the transverse direction (X-direction) and its position in the vertical direction (Z-direction) is fixed, whereby it is slidably movable in the depth direction.

As shown in FIG. 14, the first ultrasonic transducer 3 and the second ultrasonic transducer 4 are horizontally moved up to, for example, a predetermined evacuation position in an end part of the sample stand 2 during the movement of the bar member 20 with the brush 13. Accordingly, the interference between the bar member 20 with the brush 13 and the first and second ultrasonic transducers 3 and 4 can be avoided.

Next, a modification example of the wiper will be described.

Figure 15B:
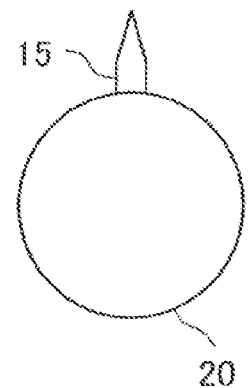

As shown in FIG. 15B, as a wiper, for example, a scraping member 15 made of rubber may be erected on the upper part of the bar member 20 in place of the brush 13. The same effects can be obtained with such a configuration.

Figure 15C:
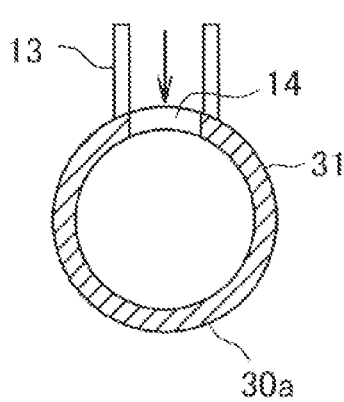

In addition, as shown in FIG. 15C, a brush 13 which can be brought into contact with the lower surface 23 of the sample stand 2 may be erected on an upper part of a suction nozzle 30a. The suction nozzle 30a shown in FIG. 15C having a circular pipe shape which is blocked at the tip end side has a cylindrical surface 31. The cylindrical surface 31 has a suction hole 14 along an axial direction of the nozzle 30a. The suction hole 14 may be an approximately rectangular hole in which a longitudinal direction is parallel to the axial direction of the nozzle 30a, or be a plurality of holes arranged in the axial direction of the nozzle 30a. According to such a configuration, bubbles brushed by the brush 13 can be immediately sucked, and thus bubbles can be more securely removed from the lower surface 23 of the sample stand 2.

Figure 15D:
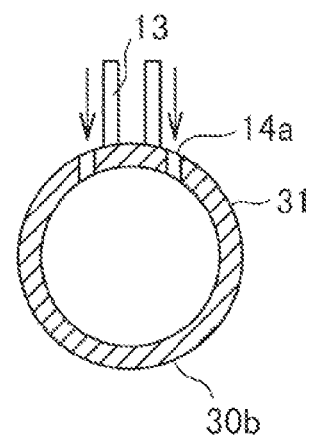

In addition, as shown in FIG. 15D, a brush 13 may be erected on an upper part of a suction nozzle 30b having a circular pipe shape, and a suction hole 14a may be formed on both sides of the brush 13 in a circumferential direction on a cylindrical surface 31 of the nozzle 30b. According to such a configuration, since the suction hole 14a is formed on the side on which bubbles are brushed by the brush 13, the bubbles can be more securely sucked from the suction hole 14a.

Figure 15E:
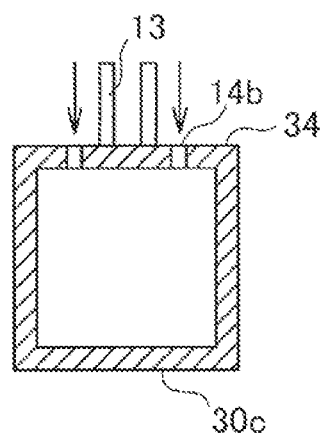

In addition, as shown in FIG. 15E, a brush 13 may be erected on an upper surface 34 of a suction nozzle 30c having a square pipe shape, and a suction hole 14b may be formed on both sides of the brush 13 in a circumferential direction on the upper surface 34 of the nozzle 30c. According to such a configuration, since the suction hole 14b is close to the lower surface 23 of the sample stand 2, bubbles can be further securely sucked from the suction hole 14b.

Figure 15F:
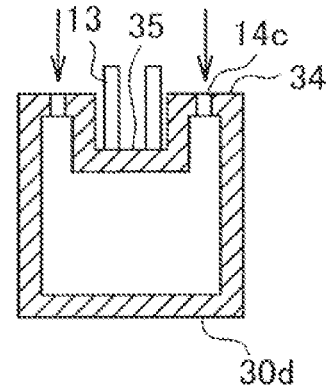

As shown in FIG. 15F, a brush 13 may be erected inside a concave part 35 formed on an upper surface 34 of a suction nozzle 30d having a square pipe shape, and a suction hole 14c may be formed on both sides of the brush 13 in a circumferential direction on the upper surface 34 of the nozzle 30d. According to such a configuration, since the suction hole 14c is yet closer to the lower surface 23 of the sample stand 2, bubbles can be further securely sucked from the suction hole 14c.

Sixth Embodiment

Figure 16:
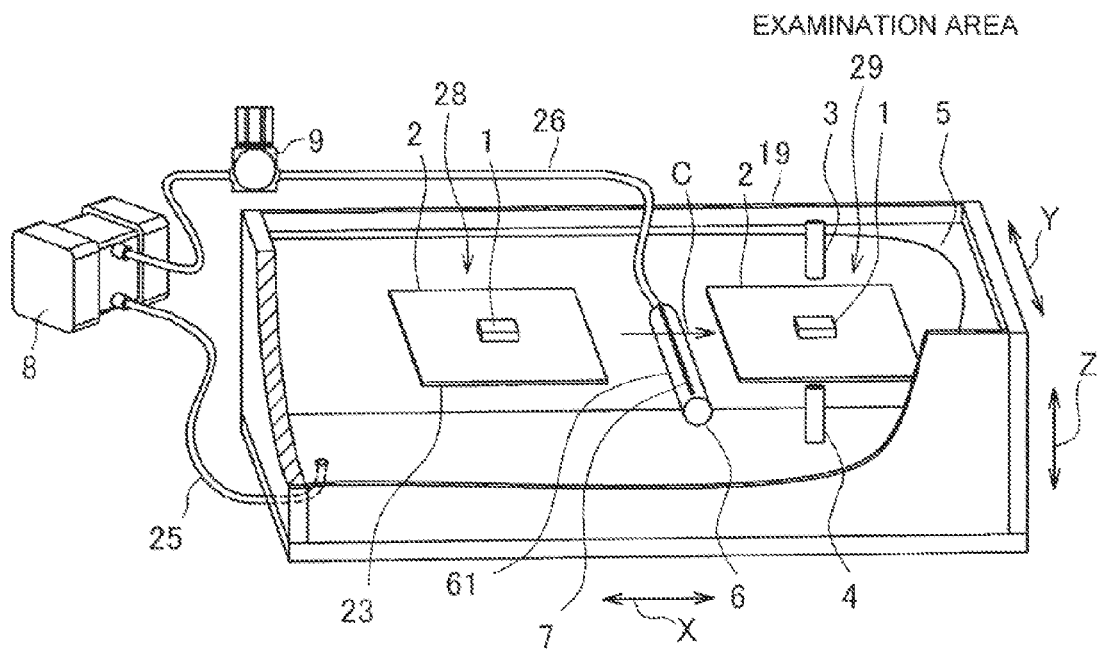
FIG. 16 is a partially cut-away perspective view schematically showing the appearance of a scanning acoustic tomograph according to a sixth embodiment of the invention.
Figure 17:
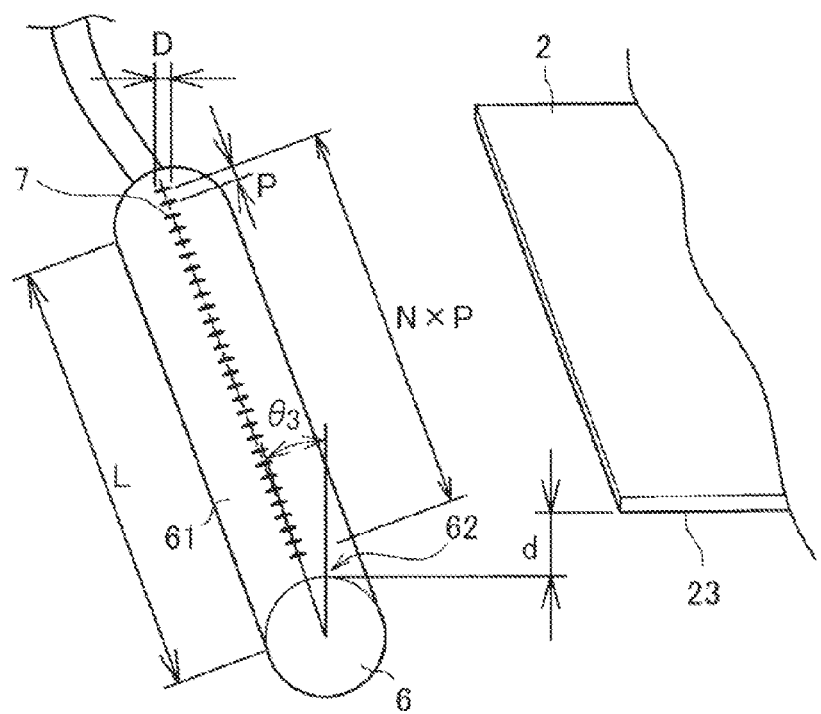
FIG. 17 is an enlarged perspective view of the nozzle shown in FIG. 16 and therearound.

Next, a scanning acoustic tomograph according to a sixth embodiment of the invention will be described with reference to FIGS. 16 and 17 by focusing on differences from the above-described second embodiment, and the description regarding the common points will be appropriately omitted. FIG. 16 is a partially cut-away perspective view schematically showing the appearance of a scanning acoustic tomograph according to the sixth embodiment of the invention. FIG. 17 is an enlarged perspective view of the nozzle shown in FIG. 16 and therearound.

As shown in FIG. 16, the scanning acoustic tomograph according to the sixth embodiment has a bubble removing area 28 which removes bubbles from a sample stand 2 and an examination area 29 which is a destination to which the sample stand 2 is moved when ultrasonic examination is performed. The sample stand 2 is supported on, for example, a rail (not shown) and can be manually or automatically moved in a C-direction from the bubble removing area 28 to the examination area 29.

In addition, the scanning acoustic tomograph according to the sixth embodiment has a nozzle 6 as an emission part which emits water 5 toward a lower surface 23 of the sample stand 2, and in the sixth embodiment, the nozzle 6 is disposed on the side of the examination area 29 of the bubble removing area 28.

As shown in FIG. 17, emission holes 7 formed on a cylindrical surface 61 of the nozzle 6 are formed at an angular position inclined to the left in an X-direction in FIG. 16, that is, to the sample stand 2 set in the bubble removing area 28 by an angle $\theta_3$ (emission angle $\theta_3$) in a circumferential direction with respect to an apex part 62 of the cylindrical surface 61.

In such a sixth embodiment, the water 5 is emitted from the emission holes 7 provided in the nozzle 6 by operating the pump 8. When the water 5 is emitted toward the lower surface 23 of the sample stand 2 set in the bubble removing area 28, a water flow is generated along the lower surface 23 of the sample stand 2, and bubbles remaining on the lower surface 23 can thus be more efficiently blown and removed. At this time, since the nozzle 6 is disposed on the side of the examination area 29 of the bubble removing area 28, bubbles can be blown to the side opposite to the examination area 29, and thus there are no adverse effects on the ultrasonic examination in the examination area 29. Moreover, as in the first embodiment, since a hydrophilic film 22 is formed on the lower surface 23 of the sample stand 2, it is difficult for the blown bubbles to re-adhere to the sample stand 2.

After the operation of the nozzle 6, the sample stand 2 on which a subject 1 is placed is moved up to the examination area 29 in the C-direction. Next, a first ultrasonic transducer 3 irradiates ultrasonic waves toward the subject 1 on the sample stand 2 moved to the examination area 29, and in order to examine the internal part of the subject 1, the first ultrasonic transducer 3 and a second ultrasonic transducer 4 are moved horizontally with respect to the sample stand 2 to perform scanning over the subject 1.

The emission angle $\theta_3$ of the water, a diameter D, a pitch P, and a number N of the emission holes 7, a distance d in a vertical direction (Z-direction) between the lower surface 23 of the sample stand 2 and the nozzle 6, and an entire length L of the nozzle 6 may be set to experimentally appropriate values, respectively, and are not particularly limited.

According to this sixth embodiment, it is possible to conduct a bubble removing operation of the next subject 1 in the bubble removing area 28 during the ultrasonic examination in the examination area 29. In addition, since the subject 1 placed on the sample stand 2 subjected to the removal of bubbles is moved up to the examination area 29 in the water 5 without being moved to the outside from the water 5 which is an ultrasonic transmission medium, the ultrasonic examination can be very efficiently conducted.

Here, as shown in FIG. 16, the nozzle 6 is disposed in parallel with the sample stand 2 in a depth direction (Y-direction), but is not limited thereto. The nozzle 6 may be disposed in parallel in the transverse direction (X-direction).

In addition, the nozzle 6 may be configured to be movable with respect to the sample stand 2. For example, in the case of FIG. 16, the nozzle 6 can be configured so that it is disposed in parallel in the depth direction (Y-direction) and its position in the vertical direction (Z-direction) is fixed, whereby it is slidably movable in the transverse direction (X-direction). The nozzle 6 is moved from the side of the examination area 29 of the bubble removing area 28 (initial position) to the left in the X-direction in FIG. 16 to remove bubbles, and then returns to the initial position. According to such a configuration, the water 5 can be securely emitted over a wide range of the lower surface 23 of the sample stand 2 set in the bubble removing area 28, and thus bubbles remaining on the lower surface 23 can be more efficiently blown and removed to the side opposite to the examination area 29.

In addition, any of the configurations of the above-described first to fifth embodiments may be applied as the configuration in which bubbles are removed from the lower surface 23 of the sample stand 2 in the bubble removing area 28 of the sixth embodiment.

Figure 18:
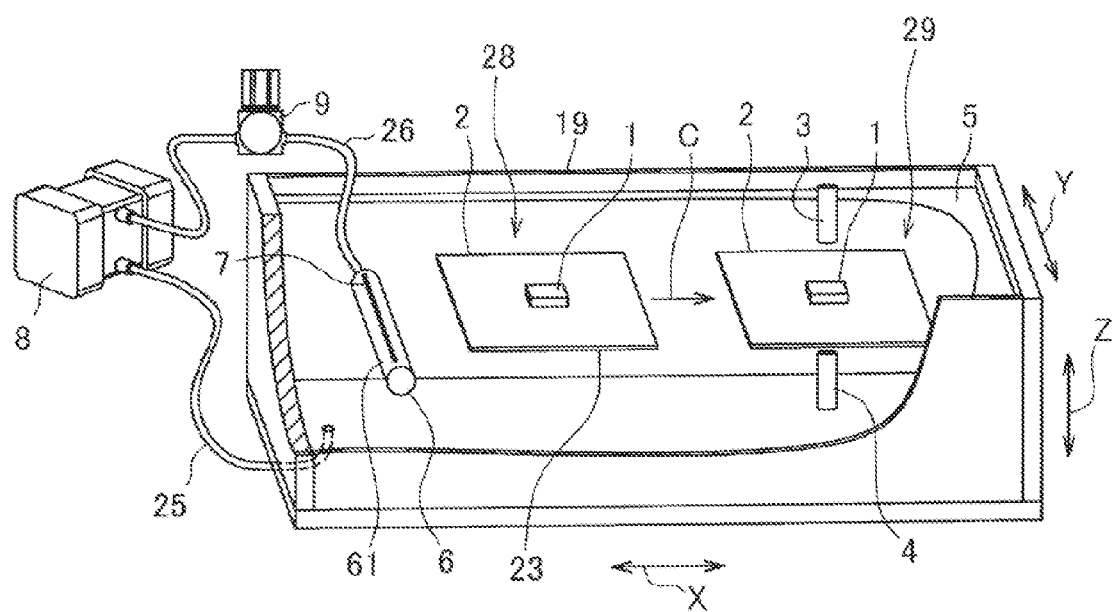
FIG. 18 is a partially cut-away perspective view schematically showing the appearance of a scanning acoustic tomograph according to a modification example of the sixth embodiment of the invention.

FIG. 18 is a partially cut-away perspective view schematically showing the appearance of a scanning acoustic tomograph according to a modification example of the sixth embodiment of the invention.

In the modification example of the sixth embodiment shown in FIG. 18, the nozzle 6 is disposed on the side opposite to the side of the examination area 29 of the bubble removing area 28. As in the scanning acoustic tomograph shown in FIG. 16, the emission holes 7 formed on the cylindrical surface 61 of the nozzle 6 are formed at an angular position inclined to the left in an X-direction in FIG. 18 (to the side opposite to the sample stand 2 in FIG. 18) by an angle $\theta_3$ (see FIG. 17) in a circumferential direction with respect to the apex part of the cylindrical surface 61.

In the case of the modification example of the sixth embodiment, the nozzle 6 is configured so that it is disposed in parallel in a depth direction (Y-direction) and its position in a vertical direction (Z-direction) is fixed, whereby it is slidably movable in the transverse direction (X-direction). The nozzle 6 is moved from the side opposite to the examination area 29 of the bubble removing area 28 (initial position) to the right in the X-direction in FIG. 16 to remove bubbles, and then returns to the initial position. According to such a modification example of the sixth embodiment, the water 5 can be securely emitted over a wide range of the lower surface 23 of the sample stand 2 set in the bubble removing area 28, and thus bubbles remaining on the lower surface 23 can be more efficiently blown and removed to the side opposite to the examination area 29.

Seventh Embodiment

Figure 19:
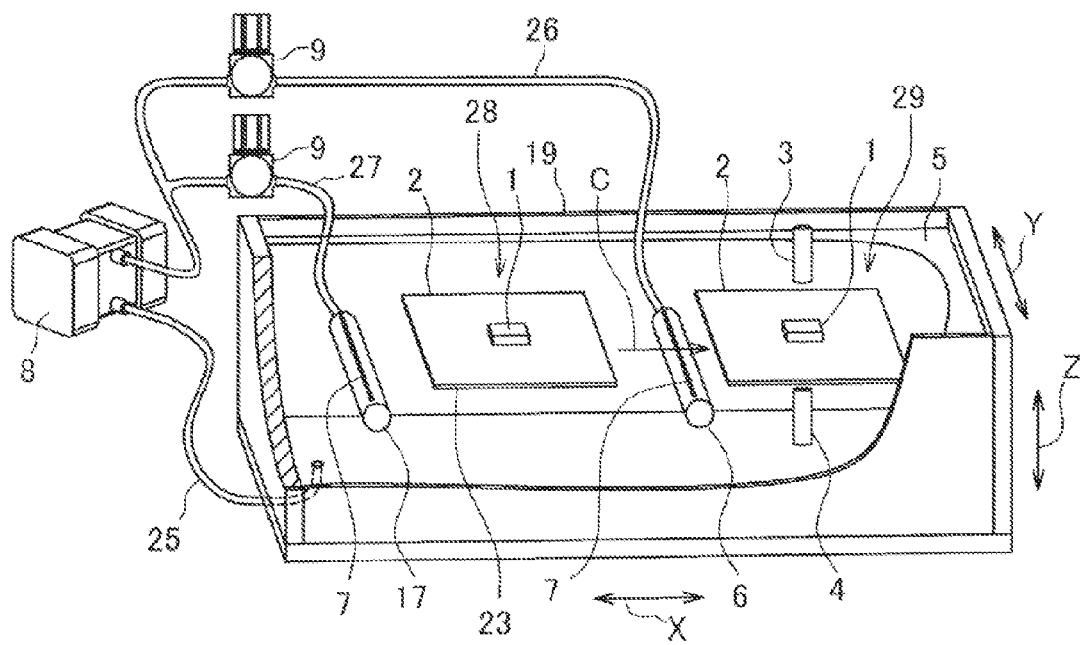
FIG. 19 is a partially cut-away perspective view schematically showing the appearance of a scanning acoustic tomograph according to a seventh embodiment of the invention.

Next, a scanning acoustic tomograph according to a seventh embodiment of the invention will be described with reference to FIG. 19 by focusing on differences from the above-described sixth embodiment, and the description regarding the common points will be appropriately omitted. FIG. 19 is a partially cut-away perspective view schematically showing the appearance of a scanning acoustic tomograph according to the seventh embodiment of the invention.

As shown in FIG. 19, the scanning acoustic tomograph according to the seventh embodiment is different from the scanning acoustic tomograph according to the sixth embodiment shown in FIG. 16 in that a nozzle 17 is further provided as a second emission part which emits water toward a subject 1 before placing on a sample stand 2. The nozzle 17 is installed separately from an emission nozzle 6 which emits water 5 toward a lower surface 23 of a sample stand 2, but the configuration thereof is the same as that of the nozzle 6. The nozzle 17 is connected to a pump 8 via a pipe 27, and a pressure adjuster 9 is installed in the middle of the pipe 27.

In the seventh embodiment, bubbles which adhere to the subject 1 by being trapped when the subject 1 is dipped in the water 5 from the air are removed by generating a water flow by emitting the water from the emission nozzle 17 separately provided, and then the subject 1 is placed on the sample stand 2.

According to such a seventh embodiment, bubbles adhering not only to the subject 1, but also to the sample stand 2 can be further reduced. In addition, the nozzle 17 for removing bubbles from the subject 1 in advance is separately installed, and thus the bubble removing operation itself for the sample stand 2 described in the above-described first to sixth embodiments can be reduced. In addition, the nozzle 17 is used in combination with the respective configurations of the first to sixth embodiments, and thus bubbles can be more securely removed.

Figure 20:
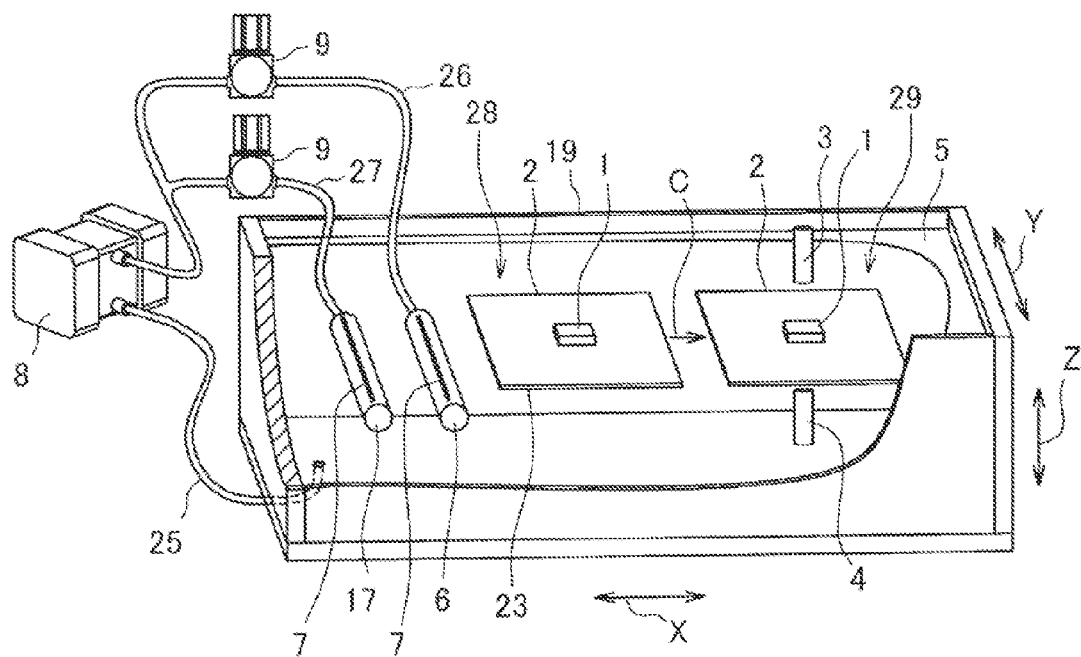
FIG. 20 is a partially cut-away perspective view schematically showing the appearance of a scanning acoustic tomograph according to a modification example of the seventh embodiment of the invention.

FIG. 20 is a partially cut-away perspective view schematically showing the appearance of a scanning acoustic tomograph according to a modification example of the seventh embodiment of the invention.

In the modification example of the seventh embodiment shown in FIG. 20, a nozzle 17 as a second emission part which emits water toward a subject 1 before placing on a sample stand 2 is added to the modification example of the sixth embodiment shown in FIG. 18. In the modification example of the seventh embodiment, bubbles which adhere to the subject 1 by being trapped when the subject 1 is dipped in the water 5 from the air are removed by generating a water flow by emitting the water from the emission nozzle 17 separately provided, and then the subject 1 is placed on the sample stand 2. Accordingly, bubbles adhering not only to the subject 1, but also to the sample stand 2 can be further reduced.

As described above, the invention has been described based on the embodiments, but is not limited to the above-described embodiments and modification example, and various modification examples are included. For example, the above-described embodiments have been described in detail in order to make the present invention easily understood, and therefore the entirety of the configuration of each of the above-described embodiments is not always indispensable for the present invention. In addition, a part of the configuration of one embodiment can be replaced with the configuration of another embodiment. In addition, the configuration of one embodiment can be added to the configuration of another embodiment. In addition, regarding some of the configurations of the embodiments, the addition of other configurations, the elimination, and the replacement are possible.

For example, the installation positions of the first ultrasonic transducer 3 and the second ultrasonic transducer 4 may be vertically reversed. In addition, a configuration in which the first ultrasonic transducer 3 and the second ultrasonic transducer 4 perform scanning over the subject 1 by moving the sample stand 2 horizontally with respect to the first ultrasonic transducer 3 and the second ultrasonic transducer 4 can also be employed.

What is claimed is:
1. A scanning acoustic tomograph comprising:
a water tank which accommodates water;
a sample stand which is disposed in the water tank and on which a subject is placed; and
a first ultrasonic transducer which irradiates ultrasonic waves toward the subject and a second ultrasonic transducer which receives the ultrasonic waves transmitted through the subject, the first and second ultrasonic transducers disposed opposed to each other in a vertical direction, wherein a hydrophilic film is formed on a lower surface side of the sample stand.

2. The scanning acoustic tomograph according to claim 1, wherein an emission part which emits water toward the lower surface of the sample stand is provided.

3. The scanning acoustic tomograph according to claim 2, wherein the emission part is configured to be movable with respect to the sample stand.

4. The scanning acoustic tomograph according to claim 3, wherein a suction part which sucks a fluid present on the lower surface side of the sample stand is provided.

5. The scanning acoustic tomograph according to claim 4, wherein the suction part is configured to be movable with respect to the sample stand in conjunction with the emission part.

6. The scanning acoustic tomograph according to claim 5, wherein an examination area to which the sample stand is moved when the examination is performed is provided, and
wherein the first ultrasonic transducer irradiates ultrasonic waves toward the subject on the sample stand moved to the examination area.

7. The scanning acoustic tomograph according to claim 3, wherein an examination area to which the sample stand is moved when the examination is performed is provided, and
wherein the first ultrasonic transducer irradiates ultrasonic waves toward the subject on the sample stand moved to the examination area.

8. The scanning acoustic tomograph according to claim 4, wherein an examination area to which the sample stand is moved when the examination is performed is provided, and
wherein the first ultrasonic transducer irradiates ultrasonic waves toward the subject on the sample stand moved to the examination area.

9. The scanning acoustic tomograph according to claim 2, wherein a suction part which sucks a fluid present on the lower surface side of the sample stand is provided.

10. The scanning acoustic tomograph according to claim 9, wherein an examination area to which the sample stand is moved when the examination is performed is provided, and
wherein the first ultrasonic transducer irradiates ultrasonic waves toward the subject on the sample stand moved to the examination area.

11. The scanning acoustic tomograph according to claim 2, wherein an examination area to which the sample stand is moved when the examination is performed is provided, and
wherein the first ultrasonic transducer irradiates ultrasonic waves toward the subject on the sample stand moved to the examination area.

12. The scanning acoustic tomograph according to claim 1, wherein a suction part which sucks a fluid present on the lower surface side of the sample stand is provided.

13. The scanning acoustic tomograph according to claim 12, wherein the suction part is configured to be movable with respect to the sample stand.

14. The scanning acoustic tomograph according to claim 13, wherein a wiper which can be brought into contact with the lower surface of the sample stand is installed in the suction part.

15. The scanning acoustic tomograph according to claim 13, wherein an examination area to which the sample stand is moved when the examination is performed is provided, and
wherein the first ultrasonic transducer irradiates ultrasonic waves toward the subject on the sample stand moved to the examination area.

16. The scanning acoustic tomograph according to claim 12, wherein an examination area to which the sample stand is moved when the examination is performed is provided, and
wherein the first ultrasonic transducer irradiates ultrasonic waves toward the subject on the sample stand moved to the examination area.

17. The scanning acoustic tomograph according to claim 1, wherein a wiper which is movable in contact with the lower surface of the sample stand is provided.

18. The scanning acoustic tomograph according to claim 17, wherein an examination area to which the sample stand is moved when the examination is performed is provided, and
wherein the first ultrasonic transducer irradiates ultrasonic waves toward the subject on the sample stand moved to the examination area.

19. The scanning acoustic tomograph according to claim 1, wherein an examination area to which the sample stand is moved when the examination is performed is provided, and
wherein the first ultrasonic transducer irradiates ultrasonic waves toward the subject on the sample stand moved to the examination area.

20. The scanning acoustic tomograph according to claim 19, wherein a second emission part which emits water toward the subject before placing on the sample stand is provided.

* * * * *